US012594433B2

(12) United States Patent
Henderson et al.

(10) Patent No.: US 12,594,433 B2
(45) Date of Patent: Apr. 7, 2026

(54) PATCH ANTENNA COMPRISING AN ELEMENT TO COVER A SKIN OF A USER

(71) Applicant: Remedee Labs, Montbonnot-Saint-Martin (FR)

(72) Inventors: James Richard Henderson, Saffron Walden (GB); Marcus Christopher Walden, Saffron Walden (GB); Pierre-Yves Sibue, Jarrie (FR); Michael Foerster, Corenc (FR)

(73) Assignee: Remedee Labs (FR)

( * ) Notice: Subject to any disclaimer, the term of this patent is extended or adjusted under 35 U.S.C. 154(b) by 644 days.

(21) Appl. No.: 17/915,912

(22) PCT Filed: Mar. 30, 2021

(86) PCT No.: PCT/EP2021/058235
§ 371 (c)(1),
(2) Date: Sep. 29, 2022

(87) PCT Pub. No.: WO2021/198221
PCT Pub. Date: Oct. 7, 2021

(65) Prior Publication Data
US 2024/0216711 A1      Jul. 4, 2024

(30) Foreign Application Priority Data

Apr. 3, 2020    (EP) ...................................... 20315103
Apr. 3, 2020    (FR) ...................................... 2003369

(51) Int. Cl.
| | |
|---|---|
| *A61N 5/04* | (2006.01) |
| *H01Q 1/27* | (2006.01) |
| *H01Q 9/04* | (2006.01) |
| *H01Q 21/06* | (2006.01) |

(52) U.S. Cl.
CPC ............... *A61N 5/04* (2013.01); *H01Q 1/273* (2013.01); *H01Q 9/0407* (2013.01); *H01Q 21/065* (2013.01)

(58) Field of Classification Search
CPC ........... A61N 5/04; H01Q 1/273; H01Q 1/38; H01Q 1/27; H01Q 9/0407; H01Q 21/065; H01Q 21/06
See application file for complete search history.

(56) References Cited

U.S. PATENT DOCUMENTS

| | | | |
|---|---|---|---|
| 2010/0036369 A1 | 2/2010 | Hancock | |
| 2018/0111353 A1* | 4/2018 | Huppert | ................. B32B 5/022 |
| 2018/0294551 A1 | 10/2018 | Matthew | |

FOREIGN PATENT DOCUMENTS

| | | |
|---|---|---|
| FR | 3071162 | 3/2019 |

OTHER PUBLICATIONS

International Search Report and Written Opinion for Application No. PCT/EP2021/058235, dated Jun. 11, 2021.

* cited by examiner

*Primary Examiner* — Ankit D Tejani
*Assistant Examiner* — Joshua Brendon Solomon
(74) *Attorney, Agent, or Firm* — C. Tumey Law Group PLLC

(57) ABSTRACT

The invention deals with a patch antenna (28) for a near field radiation. The patch antenna comprises an element (52) that has a surface intended to cover a skin of a user. Furthermore, the element (52) intended to cover the skin is arranged to make the impedance of the antenna (28) matching an impedance of skin.

10 Claims, 6 Drawing Sheets

28

22

39

22

46

26

ASIC

ASIC

42

44

28

PATCH ANTENNA COMPRISING AN ELEMENT TO COVER A SKIN OF A USER

The invention deals with radiating electromagnetic waves towards a human subject. It particularly deals with a patch antenna for a near field radiation of millimeter waves.

We know from the prior art, according to the patent application FR1758634 under the name of the applicant, a patch antenna comprising an array of patches and able to radiate millimeter waves with a power density superior to 0.5 mW/cm$^2$ to at least 2.5 continuous square centimeters of the surface of the skin of a user. This antenna is powered by application-specific integrated circuits ("ASIC"s) in a device to radiate millimeters waves towards the skin in a therapeutic goal, in particular to cure chronic pain.

However, the efficiency of the antenna, i.e the ratio between the transmission of the waves to the skin and the power provided by the ASIC's, is low. Furthermore, test protocols are adapted to the antenna radiating towards air, not towards skin. The testability of the antenna is thus difficult.

An object of the invention is notably to improve the efficiency of the antenna. Another object is to improve the testability of the antenna.

To this end, it is provided according to the invention a patch antenna for a near field radiation, comprising an element having a surface intended to cover a skin of a user, the element being arranged to make the impedance of the antenna matching an impedance of skin.

By antenna, we mean an antenna network, a radiating patch or more generally any component or set of components directly associated with the emission of radiation. Without the element intended to cover the skin, the antenna is suitable for transmitting electromagnetic radiation outside to air and can be tested with classical protocols. With the element, as this latter behaves as an impedance transformer, the impedance of the antenna is adapted to the impedance of the skin of the user, such that losses of transmission are avoided and the efficiency of the antenna radiating to the skin is greatly improved. Thus, the performance of the antenna and its testability are improved.

Preferably, the element comprises, when an electromagnetic wave crosses the element at a frequency of 61.25 gigahertz, an intrinsic impedance value situated between the intrinsic impedance value of air and the intrinsic impedance value of the dry skin deduced from its complex permittivity of 8-j11 ohms.

Thus, the impedance transformation is performed by designing the element such that its intrinsic impedance value is situated between the impedance of air and the impedance of a dry skin. The impedance of the element thus plays the role of an intermediary between the impedance of air, for which the antenna without the element is arranged, and the impedance of the skin, to which the antenna radiates across the element.

Advantageously, the element comprises a bio-compatible material.

Thus, the element is adapted to a sustainable contact with the skin of a user.

Preferably, the element comprises only polycarbonate, a thickness value of the element being situated between 0.5 mm and 3 mm, the thickness value being preferably 0.6 mm or 0.6 mm plus an integer multiple of a half wavelength when the electromagnetic wave crosses the element.

Thus, the thickness of the element is arranged such that the impedance of the element is as appropriate as possible while the element is taking minimum space.

Advantageously, the element comprises a dielectric constant value less or equal to 4 and a dissipation factor less or equal to 0.2.

These are ranges of values relevant to the impedance of the element, so that the element plays its full role as an impedance adapter between the antenna and the skin.

Preferably, the antenna comprises a main surface value equal or less than 10 cm$^2$.

Thus, the antenna is particularly small and can therefore be easily integrated into an electromagnetic radiation transmission module.

Advantageously, the antenna comprises at least eight patch devices to radiate electromagnetic waves, the devices being situated on a same substrate and separated from each other by a distance value situated between 2.4 and 2.5 mm, the eight devices being able to expose to electromagnetic radiation between 0.625 cm$^2$ and 1 cm$^2$ of a continuous surface.

Thus, the patch devices are the radiating elements of the antenna. In other words, the antenna is an antenna network, each patch being able to be considered as an indivisible antenna of this network. These patches are arranged so that the antenna network exposes a continuous surface to the radiation. The distances between the patch devices correspond to half a wavelength of a wave emitted to an empty space around 60 gigahertz, so as to further improve the efficiency of the antenna, as well as the uniformity of its radiation.

Preferably, in order to improve the homogeneity of the radiation, the patch devices are arranged in order to radiate in phase.

Advantageously, the antenna comprises a printed circuit board having a substrate, the substrate comprising a dielectric constant value between 2.9 and 3.1 and a dissipation factor value between 0.0010 and 0.0020 when an electromagnetic wave crosses the element at a frequency of 61.25 gigahertz, a thickness value of a layer of the substrate having a thickness value between 0.1 and 0.6 mm, preferably between 0.2 and 0.3 mm, a total substrate assembled thickness being situated between 0.5 and 1.6 mm.

These features improve the efficiency of the radiation emitted by the antenna.

Preferably, the antenna comprises via fences at all the borders of the substrate, the vias of the fences having a diameter value greater than or equal to 175 micrometers, a pitch value between vias being superior or equal to 300 micrometers.

In this way, the number of vias required is reduced compared to the number of vias which would be required if they were smaller, and the production cost is therefore reduced.

Advantageously, a cavity being formed by the via fences, the cavity is arranged such that a resonant frequency value of the cavity is outside a frequency range going from 55 to 65 gigahertz.

Thus, the waves emitted are not disturbed by the cavity. To achieve this adaptation, positioning adjustments of the vias are possible.

Furthermore, according to the previously mentioned patent application FR1758634 in the name of the applicant, it is already known a bracelet capable of emitting millimeter waves comprising a surface density of power greater than 0.5 mW/cm$^2$ at the patient's wrist, in particular with the aim of treating the patient's chronic pain. The bracelet includes a wave emission module, which includes four application-specific integrated circuits (ASICs) dedicated to the generation of millimeter wave radiation. Each of these circuits feeds four planar antennas with radiation. These antennas allow continuous wave exposure of 2.5 centimeters of the patient's wrist skin surface. The dimensions of said module, integrated into the bracelet, are 37 millimeters in length, 20 millimeters in width and 3 millimeters in thickness.

However, due to these dimensions, this rigid module integrated into the bracelet cannot optimally conform to the shape of the patient's wrist, so that air gaps form between the skin and the bracelet, reducing the efficiency of the antenna radiation. In addition, these dimensions make its mechanical integration within the bracelet delicate.

Therefore, another goal of the invention is to improve the efficiency of the radiation emitted by the module. Another object of the invention is to facilitate the mechanical integration of the module within a device, in particular within a bracelet Therefore it is also provided by the invention an electromagnetic wave emission module, the module having a total volume of less than 1 cubic centimeter and comprising at least one electromagnetic waves radiation source connected to at least one emission antenna, the emission antenna being able, when the module is arranged at a surface, to emit electromagnetic waves having a power density of at least 0.5 milliwatt per square centimeter of surface.

Thus, the module is particularly small, so that it can be integrated into a portable device in a simpler manner. In addition, its small dimensions allow it to more optimally match the rounded shape of a patient's skin, such as the circumference of a wrist or ankle, so that the efficiency of the emission is improved. Finally, with a single radiation source instead of four, the manufacturing cost of the module is reduced.

Advantageously, the surface being a skin, the emission antenna comprises an element having a surface intended to cover the skin.

Thus, this small volume also includes the presence of this protective element of the antenna which is intended to make the link between the antenna and the skin and which can be called a radome. It is placed between the emission antenna and the surface to which the waves are transmitted.

Preferably, the waves have a power density value situated between 5 and 35 milliwatts per square centimeter of surface.

It is a particularly efficient power band for the treatment of the chronic pain of a patient with millimeter waves. Furthermore, legal standards oblige to limit the power density of the waves, so that the module can be controlled so as not to exceed a given threshold if necessary.

Advantageously, the waves have a frequency value between 3 and 120 gigahertz, preferably between 55 and 65 gigahertz.

It is a particularly efficient frequency band for a treatment with millimeter waves.

Preferably, the radiation source is an application specific integrated circuit ("ASIC") having a total volume value of less than 5 cubic millimeters, and being able, when it is electrically powered, of generating the radiation emitted by the emission antenna.

Thus, the radiation source has particularly small dimensions while being able to generate radiation with adequate properties.

Advantageously, the emission antenna comprises a planar antenna or a network of planar antennas, a value of a main surface of the planar antenna or of the network of planar antennas being between 0.5 and 2 cm$^2$, the planar antenna or the network of planar antennas being able, when it is powered by the radiation generated by the radiation source, to emit the radiation towards the surface.

Thus, the antenna has particularly small dimensions, so that it can be easily integrated into the module while optimally exposing the patient's skin to the waves that the antenna emits. Indeed, its miniaturization makes it possible to avoid generating an air gap between the antenna and the skin of a patient, even on a rounded portion such as a wrist of the patient.

Preferably, the radiation source is connected to at least four distinct emission antennas.

These four antennas may notably be four patch devices or planar devices able to radiate waves. Thus, the source is powerful enough to power the four planar antennas alone.

Advantageously, the radiation source is connected to eight distinct emission antennas.

Thus, the source is powerful enough to power the eight antennas alone. This further reduces the cost of manufacturing the module, in comparison with a module having a radiation source for four emission antennas and therefore two sources for eight antennas. This also facilitates mechanical integration of the module, since the presence of a single source for eight antennas, instead of two sources, saves space.

Preferably, the module comprises two separate radiation sources, each of them being connected to eight separate emission antennas.

Thus, the antennas are divided into two groups of eight antennas each, each group having its own source of radiation. This arrangement allows a gain of modularity, as each group can be assembled separately before being integrated into the transmission module.

Advantageously, at least some of the antennas form a network of antennas connected to each other.

Thus, the powering of the antennas is simplified by the fact that the antennas of a network are connected to each other. A radiation source can therefore be connected to the circuit at a single point to power all of the antennas in the network. In particular, a network can be formed of eight separate antennas, so that a single ASIC powered a whole network. In this way, a module then comprises two ASICS and two separate networks.

Preferably, the module comprises:

a frequency generator able to generate a reference frequency, a frequency measuring device able to measure a frequency deduced from the frequency of the radiation emitted by the radiation source, and a frequency comparator able to compare the deduced frequency with the reference frequency.

Thus, it can be verified that the frequency of the radiation conforms to the chosen frequency of the radiation. Indeed, as the radiation and its frequency are generated inside the radiation source, without absolute frequency reference as for example with a quartz, the frequency of this radiation is subject to the tolerances of the manufacturing techniques as well as to temperature changes. A much lower reference frequency is therefore generated outside the radiation source, and it is compared with a frequency deduced, also much lower, from the frequency of the radiation, in order to verify whether the latter is indeed the one that was chosen. In other words, we measure a frequency deduced from the radiation frequency which allows us to verify that the latter is the correct one.

It is also provided according to the invention a portable device for transmitting electromagnetic waves, comprising at least two modules as described above and an electrical power source for electrically powering the modules.

Thus, the portable device allows the emission of waves to the skin of a patient, and without physical constraint on the patient, who can be at home, outside, in motion, etc. The presence of two modules of small dimensions rather than one of larger dimensions makes it possible to facilitate the mechanical integration of the modules, and to improve the efficiency of the radiations. Indeed, on rounded parts such as a wrist, the two small modules, distinct even distant from each other, will better fit the shape of the skin than a single rigid module of larger dimensions. This separation of a module into two separate smaller modules thus makes it possible to reduce or even avoid the formation of an air gap between the modules and the patient's skin, while retaining the same exposure surface as a single module and with radiation of electromagnetic waves having the same properties.

Advantageously, the modules are arranged so as to expose non-adjacent respective areas of the surface to electromagnetic waves.

Thus, unlike a single module that exposes to the waves a continuous surface, the division of the module into two smaller modules makes it possible to expose distinct areas of the surface, even if the value of the total surface exposed to the waves remains the same.

Preferably, the device is able to expose to the waves simultaneously in total at least 1 square centimeter of the surface, preferably at least 2.5 square centimeters of the surface.

Thus, although each module is smaller, the total area of the surface exposed to the two modules is at least equal to 2.5 square centimeters, which is a sufficient area to obtain a therapeutic effect for the treatment of chronic pain. However, it is possible to deactivate one of the two modules, the therapeutic effect then being able to persist by the emission of waves from a single module, that is to say for an exposed surface of 1.25 square centimeters, or even of 1 square centimeter.

Advantageously, each module is electrically connected to the electrical power source by respective flexible means of electrical connection.

Thus, the flexible nature of the connection means allows the modules to be placed in a wider range of position than if the connection means were rigid. In particular, each module can be placed near an area of a human wrist, the areas being different from each other. In other words, the flexibility of the connection means makes it possible to place the modules independently of one another, while rigid connection means would generate much greater positioning constraints.

Preferably, the device comprises a control module for controlling the modules, the control module being distinct from the electrical power source and distinct from each transmission module, the control module being electrically connected to the electrical power source and to each transmission module by respective flexible means of electrical connection.

Thus, the control module, making it possible to control the emission modules, is distinct from these emission modules. Here again, the flexible nature of the connection means makes it possible to facilitate the integration of all of the elements within the portable device. In particular, this makes it possible to place the elements independently of one another, whereas rigid connection means would not allow that.

Advantageously, at least some of the flexible means of electrical connection are flexible printed circuits.

Thus, the mechanical integration of the elements is further facilitated.

Preferably, the device comprising a flexible bracelet, the emission modules are arranged within the flexible bracelet so as to expose to waves different parts of a surface of a wrist.

Thus, the emission modules are distributed within the flexible portion of the bracelet so as to avoid the formation of air gap between each emission module and the wrist, in order to improve the efficiency of the radiation.

Advantageously, the device is able to be worn at least in one of the following places:

on the face
around a wrist;
on one leg;
around an ankle;
on a back;
to one ear; or
in the palm of one hand.

BRIEF DESCRIPTION OF THE FIGURES

The invention will be better understood on reading the description which provides examples and is made with reference to the attached drawings in which.

DETAILED DESCRIPTION

We will first describe embodiments and implementation of an electromagnetic wave emission module. In a second step, we will describe embodiments of an antenna for transmitting electromagnetic radiation included in the module. The antenna is particularly suitable for the transmission module presented, but it could be integrated into other devices and is therefore not intrinsically linked to the module.

I. The Emission Module

A—Components

Figure 1:
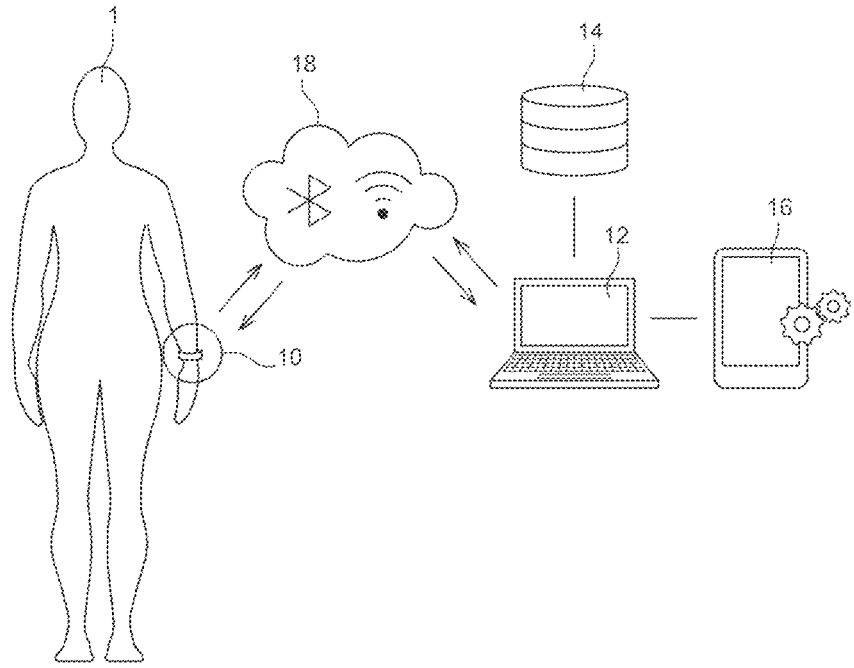
FIG. 1 is an overall diagram of a system according to an embodiment of the invention.

FIG. 1 illustrates the general framework of the invention. Patient 1 has chronic pain. He wears a device 10 according to a first embodiment and a first mode of implementation of the invention, which treats the pain by emitting electromagnetic millimeter waves towards the skin of patient 1, at his wrist. By "millimeter waves" is meant electromagnetic waves of frequency between 30 and 300 GHz, but the invention can also be extended to waves of frequency between 3 and 30 GHz.

Figure 2:
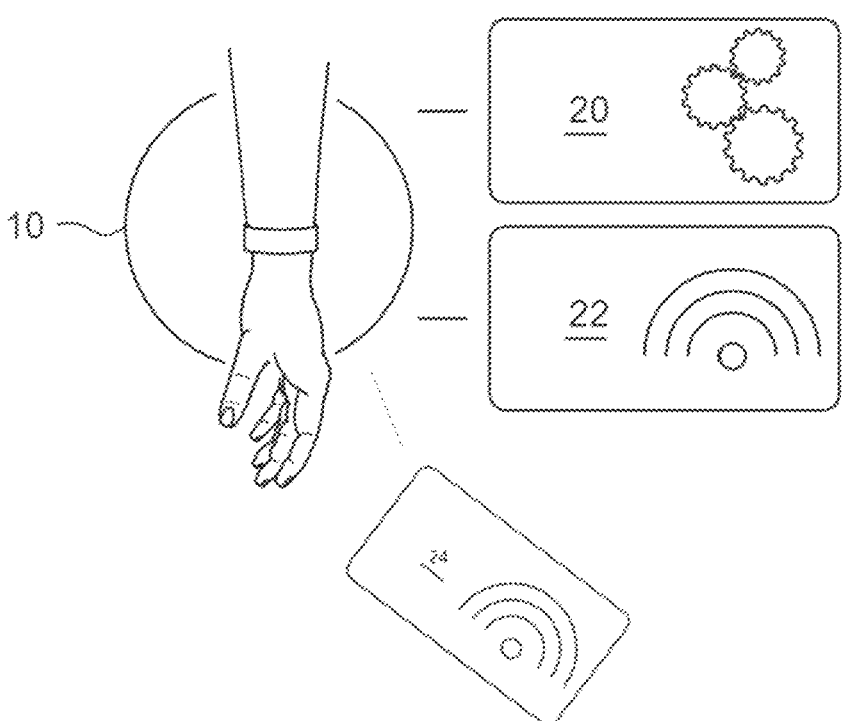
FIG. 2 is a diagram of elements of this embodiment.

In this case, this device 10 has the general shape of a wristwatch, or bracelet, and is fixed around the wrist in the same way as a watch. Illustrated in FIG. 2 schematically and in FIG. 3 in more detail, the device 10 comprises a control or command module 20 and two wave emission modules 22 and 24. The device 10 having the general shape of a watch, it can be a watch in which the modules 20, 22 and 24 would have been integrated. Conversely, the functionality of a watch could be integrated into device 10.

The control module 20 controls the transmission modules 22 and 24. The control module 20 is activated by the patient, but it can also be programmed by the patient or another user on the device 10 directly by the button 23 or via a terminal such as the computer 12. The button 23 is provided with light-emitting diodes which can be activated to indicate an event to the patient, for example a lack of battery or the operation of a particular program in progress. The control module 20 is present in the upper part of the device 10 while the millimeter wave emission modules 22 and 24 are located in the lower part and are therefore intended to be in contact with the lower skin of the wrist.

We will now describe in detail the electromagnetic wave transmission module 22 integrated in the device 10. Unless otherwise indicated, the features of the module 24 are identical, so that the explanations which follow concerning the module 22 also apply for module 24. This module can be integrated into any type of device intended to emit waves, and not only into device 10 in the shape of a wristwatch. Its applications are not limited to the treatment of pain.

Figure 4:
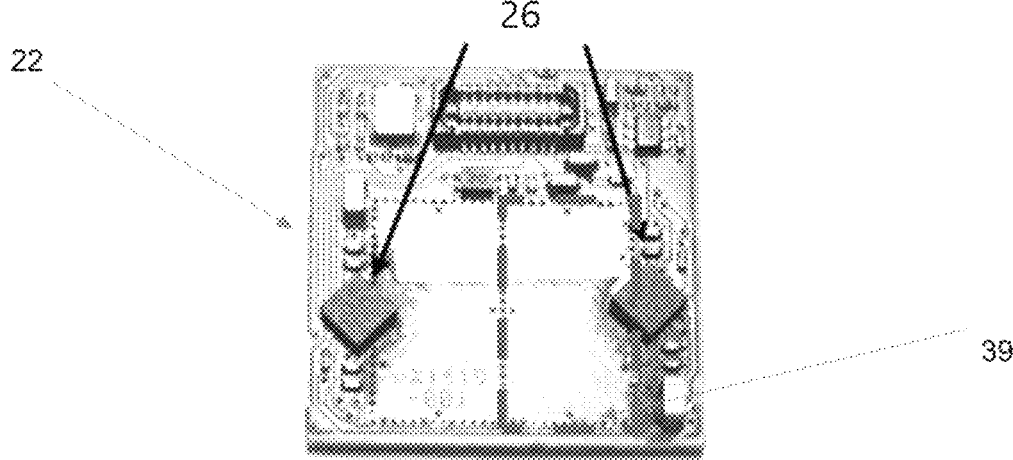
FIG. 4 is an illustration of a front of a wave emission module of this embodiment.
Figures 5, 6:
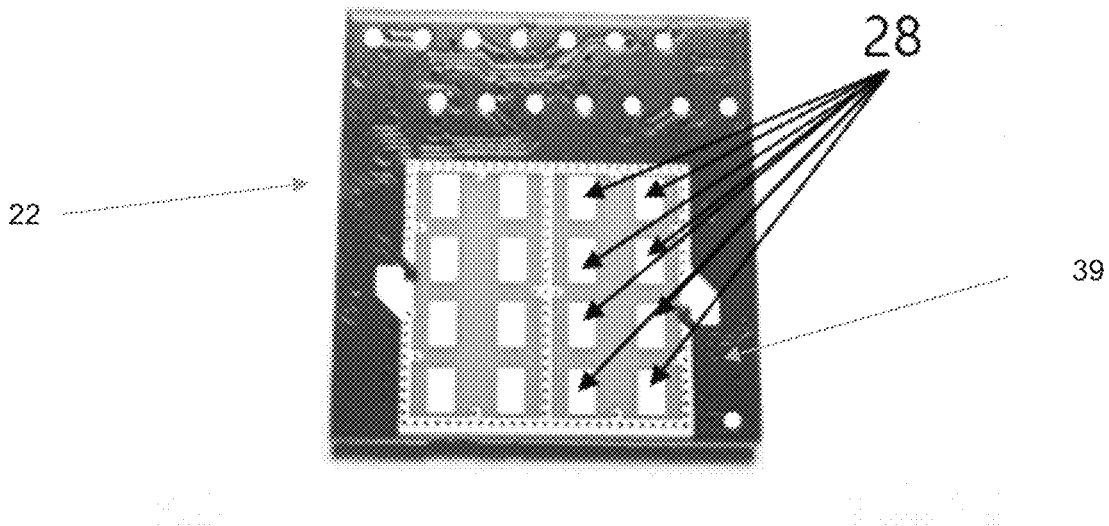
FIG. 5 is an illustration of the back of this module.
FIG. 6 is a diagram of this module.
Figure 7:
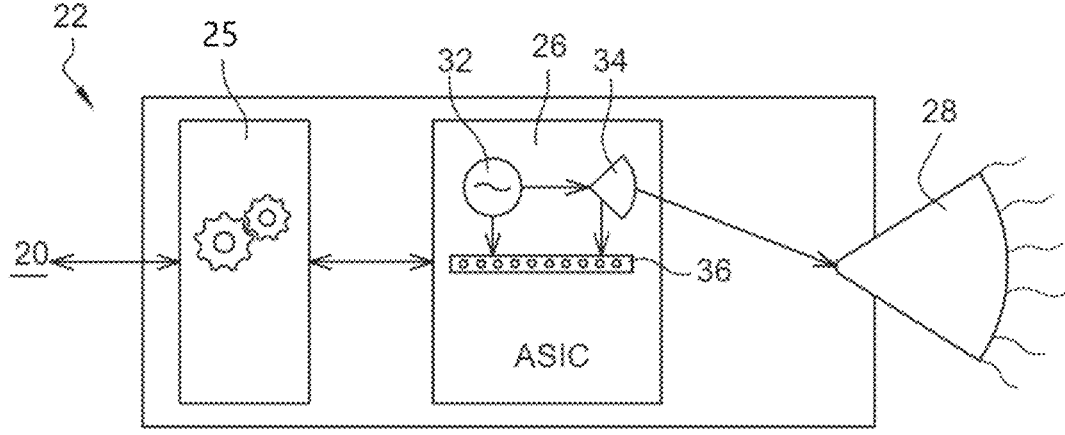
FIG. 7 is a diagram of a circuit-antenna pair of this module.
Figure 8:
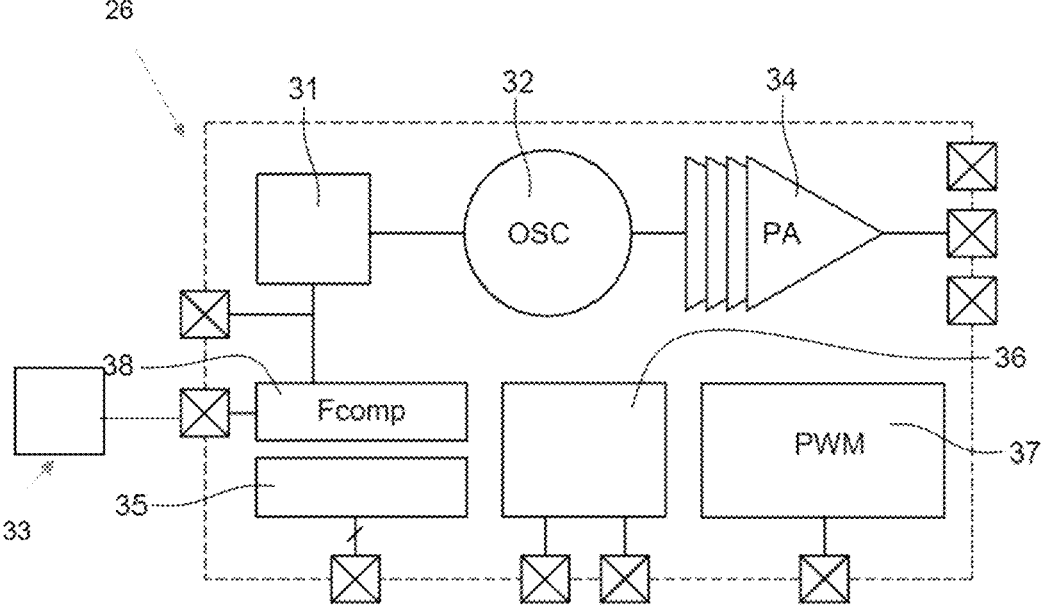
FIG. 8 is a diagram of a circuit of this couple.

This transmission module 22 illustrated in FIGS. 4 and 5, and the content of which is shown diagrammatically in FIGS. 6 to 8, has two circuit-antenna pairs 42, a heat sink 46 and a skin sensor 44. It also has (but not illustrated) a power input, a digital control member, a reference clock and a temperature sensor 49. The module 24, identical, could however have fewer elements. Thus, the skin sensor and the temperature sensor could be present in only one of the two modules.

Each of the two circuit-antenna pairs 42 has a control interface 25 in connection with the control module 20, an ASIC ("application-specific integrated circuit) 26 and a network of eight planar antennas (which can be called "patches") 28. ASIC 26 is the source of millimeter wave radiation. It is ASIC 26 which generates the radiation so that radiation is transmitted to the antenna network 28. One of the technical particularities of this arrangement with respect to application FR1758634 is the fact that a single ASIC 26 is associated with eight different antennas 28 and a separate circuit, as illustrated in FIGS. 4 and 5 which show the front and back respectively of the same module 22. The loss of power due to the presence of a single ASIC instead of several for powering these eight antennas is compensated by the improved antenna performance. The interface 25 can be located within the control module 20.

The ASIC 26, as illustrated in FIG. 7, comprises an oscillator 32, a power amplifier 34 and a digital part 36 for setting and controlling the ASIC. Illustrated in more detail in FIG. 8, it also includes a frequency divider 31, a communication bus 35, a "Pulse-width modulation" (PWM) control member 37, a reference frequency generator 33 and a comparator 38. The oscillator 32 generates the operating frequency of the ASIC. The amplifier amplifies this signal so that the desired power is available at the component output. This power is adjustable between 0 and 60 mW. The power management circuit makes it possible to power all of the component's functions correctly. The "PWM" control unit makes it possible to transmit the HF output signal continuously or discontinuously.

The frequency comparator 38 and the divider 31 make it possible to check the frequency of the radiation emitted by the ASIC 26. Actually, the oscillator 32 being internal to the ASIC 26, it is not possible to check the frequency of the radiation it generates. However, this frequency can be modified involuntarily by the other elements or by modifications of temperature. To measure it, we therefore proceed as follows: the reference frequency generator 33, which is an external oscillator, generates a signal of 10 MHz. The divider 31, on the other hand, generates, from the output radiation of the ASIC 26, a deduced signal, a sub-multiple of the one emitted to the skin, by dividing by 3840 the frequency value of the output signal. The reference signal from the generator 33 and the deduced signal from the divider 31 are then compared to each other by the comparator 38. As the frequency of the reference signal is known (10 MHz) and the frequency deduced is the result of a division by 3840 of the frequency of the output signal, this comparator 38 makes it possible to find the value of the real frequency of the output signal, with an accuracy of the order of 8 MHz. If the found frequency differs too much from what it should be, an external controller requests oscillator 32 to reduce or slightly increase its frequency. This checking thus guarantees that the output frequency will be in the chosen band, most often between 61 and 61.5 GHz. It also makes it possible to verify that the frequencies of the output signals of each ASIC are distinct, so as to avoid a phenomenon of interference fringes. Actually, in the device 10, comprising two modules 22 and 24 and therefore four ASICS 26, the output frequencies of the ASICs are adapted so that they are separated by at least 100 MHz. Thus, the four frequencies can be 61.1, 61.2, 61.3 and 61.4 GHz respectively.

The manufacturing principles of the ASIC are similar to that of the ASICs described in application FR1758634. Thus, the manufacturing of this ASIC 26 is carried out using "CMOS" ("Complementary Metal Oxide Semiconductor") technology, a technology known to those skilled in the art and which will therefore not be described in detail. More specifically, the transistors are of the "65 nanometer CMOS" type. Alternatively, they could have been developed in silicon-germanium (SiGe) or even in gallium arsenide (GaAs). On the other hand, technologies of the "gunn diode" type do not make it possible to reach the minimum size and the desired cost. The ASIC 26 thus includes a silicon integrated circuit in a BGA ("Ball Grid Array") type housing, a type of housing well known to those skilled in the art, tailor-made for ASIC 26, the housing comprising also balls (called "bump"). The frequency oscillator 32 is placed in a cavity (not shown) within the housing which aims not to disturb the generated frequency. The size of this BGA box including the ASIC is 2.2*2.2*0.9 millimeters in this case.

As illustrated in FIGS. 4 and 5, each millimeter wave transmission module 22 and 24 comprises two of these ASICs 26, each ASIC 26 being associated independently of each other with a network of eight radiating patches 28 within a circuit of its own. The ASICs 26 and the associated antenna network 28 are arranged on either side of a substrate 39. The connection of the ASICs 26 to the antennas 28 is done by means of "balls" through the substrate 39. This set of components allows to minimize the loss of electromagnetic waves. The antennas 28, having received the radiation generated by the ASIC 26 to which they are associated, emit electromagnetic waves intended for the skin of the patient 1. We will describe in more detail the substrate 39 and the antennas (or radiating patches) 28 below.

To sum up, each of the two wave emission modules 22 and 24 comprises two ASICs 26 and sixteen antennas 28 located on a substrate 39 via two separate circuits. The total size of each of these modules is 16.5 mm*17 mm*2 mm, i.e. a total surface for each module of 2.8 square centimeters of circuit and 0.56 cubic centimeters, i.e less than 3 square centimeters of surface and less than 0.6 cubic centimeters of volume. If we consider that the radome 52 of the antenna network (which will be described below) is part of it, then the module is 16.5 mm*17 mm*2.8 mm, so it has a volume less than 0.8 cubic centimeters. Finally, if we consider an assembly integrated in bracelet 10, formed by an emission module 22 or 24, a radome 52 and a thermal gap pad (conventional for those skilled in the art), this assembly is 22*20*6 mm, less than 2.7 cubic centimeters. The fact that these modules are smaller than those of the prior art makes it easier to integrate them into the device 10, and allows to improve the radiation efficiency of the antennas 28, as explained below. Another important advantage of this division of a module into two smaller modules is described below.

B—Integration by Parts

Figure 3:
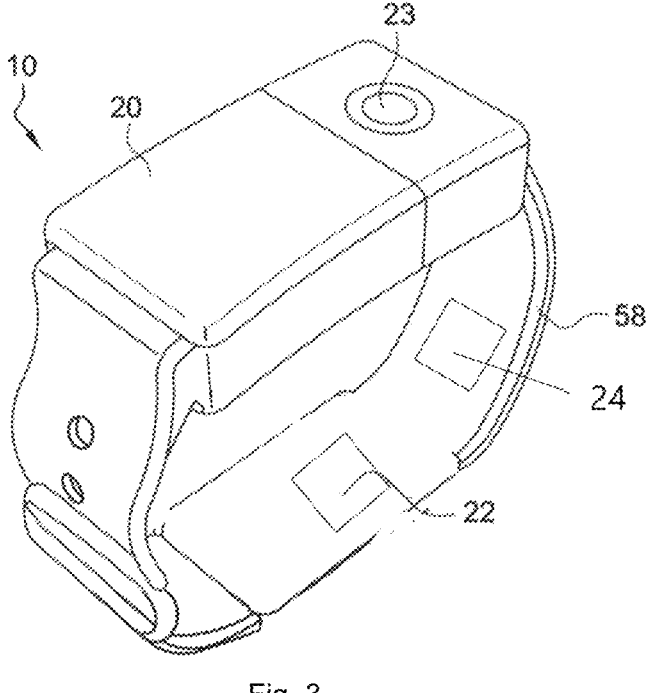
FIG. 3 is a perspective view of a device according to this embodiment.
Figure 9:
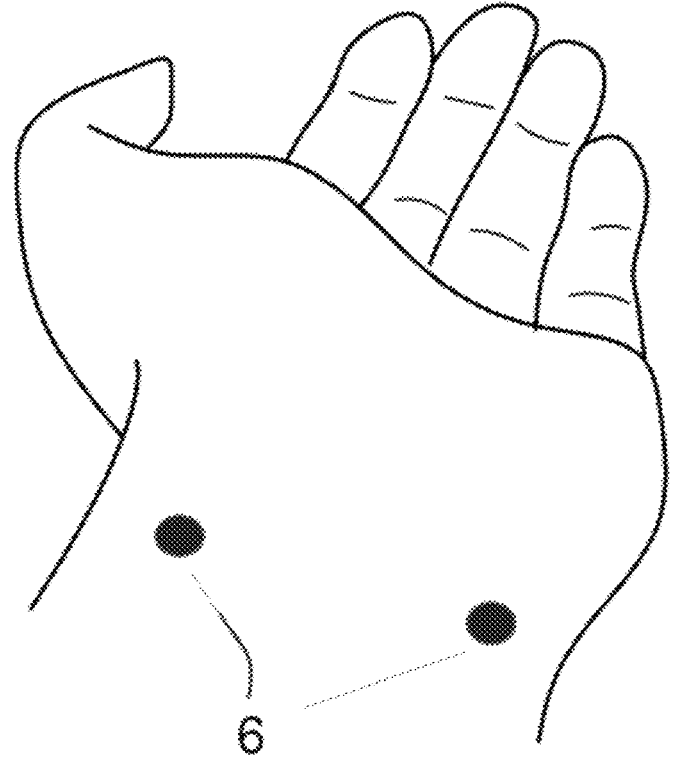
FIG. 9 is a diagram of a hand of a patient using the invention.

As illustrated in FIG. 3, the modules 22 and 24 are placed on separate locations of the bracelet 10. The emission of millimeter waves is therefore directed towards two separate portions of the patient's wrist, illustrated schematically in points 6 in FIG. 9. Since these rigid modules 22 and 24 are smaller than the ones of application FR1758634, they better conform to the rounded shape of the human wrist. Thus, the formation of air gaps between the wrist and the modules 22 and 24 is avoided, so that the radiation emitted by the sixteen antennas 28 of each module is more efficient. In other words, compared to the single module in application FR1758634, the total efficiency of the two modules 22 and 24 is improved.

Figure 10:
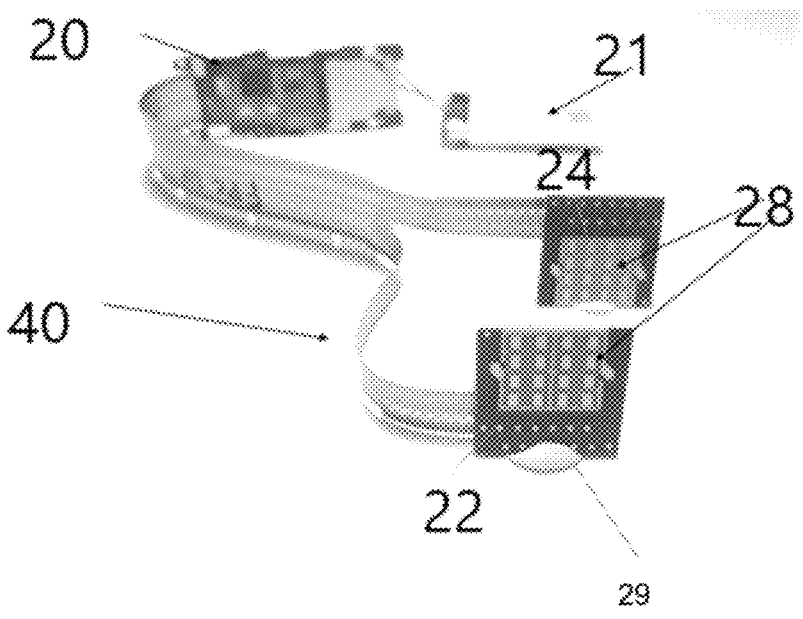
FIG. 10 is an illustration of modules connected together according to an embodiment of the invention.
Figure 11:
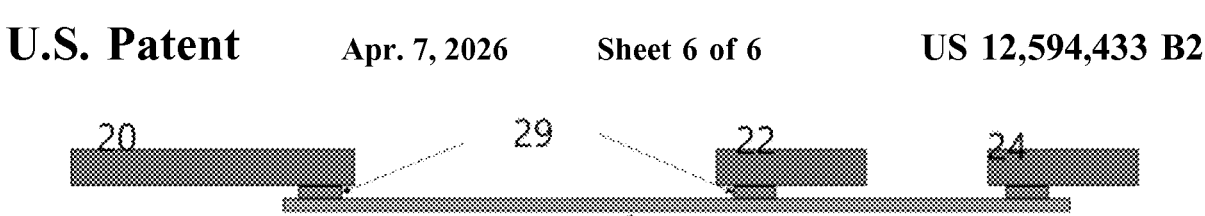
FIG. 11 is a diagram of these connections.

The mechanical integration of the wave emission modules 22 and 24 is illustrated in FIGS. 10 and 11. The control module 20, which is integrated into the top of the bracelet 10, is connected to the emission modules 22 and 24 by a flexible "flex" 40. By "flex" is meant a flexible printed circuit, also called a "flexible printed circuit", which is well known to those skilled in the art, and which makes it possible to generate electrical connections subject to twisting or other types of bending. In FIG. 10, the flex 40 comprises a single part, which is then divided into two flex parts, each of these parts being connected to one of the two wave emission modules 22 and 24. In this way, the two emission modules 22 and 24 can be integrated independently of each other within the bracelet 10, and in particular at the two distinct positions 6.

The connection between the flexes and the three elements—the control module 20, the wave emission modules 22 and 24—is made by means of electrical connectors 29 acting as intermediaries between the flexible circuit 40 and the rigid circuits of the three modules 20, 22 and 24. Furthermore, the control module 20 is connected to a battery 21. This battery thus makes it possible, via the module 20, to provide electricity to all of the components of the bracelet 10.

The integration into the device 10 of the two small wave emission modules 22 and 24, flexibly connected to the control module 20, is easier than the integration of the wave emission module from application FR1758634, whose total dimensions are those of an assembly formed by the two modules 22 and 24 which would be adjacent. In other words, mechanical integration, for the same "module volume" is easier as it is made by parts.

As a reminder, as mentioned above, the division of the module into two small modules 22 and 24 also makes it possible to avoid the presence of air gaps, since smaller surfaces of modules conform better to the rounded shape of the wrist than a larger rigid surface. Thus, whatever the radiating elements 28 of the modules, this division into two parts of the module improves the efficiency and facilitates the mechanical integration of the elements.

However, the radiating elements 28 of the module described and illustrated have also been improved in comparison with the radiating elements of the former device, so that their own performance is also more important. We will now describe these improved radiating elements 28.

II. The Antenna Network

With respect to the antenna network disclosed in application FR1758634, the one of the present invention has been improved on several points so as to increase its efficiency and testability (the ease of testing the antenna), and to reduce its manufacturing cost. Thus, for the same amount of energy provided to the skin, it is possible to emit less energy at the level of the radiation source.

A—The Substrate

Each ASIC 26 is welded onto two layers of "HF" substrate made of MT77 (from the manufacturer ISOLA), which makes it possible to limit as much as possible the losses of high frequency electromagnetic radiation. The choice of the MT77 comes from its features: a dielectric constant of 3 and a dissipation factor of 0.0017, at a frequency of 61.25 GHz. More generally, it is advantageous that the material of these substrate layers has a dielectric constant of a value between 2.9 and 3.1, and a dissipation factor of a value between 0.0010 and 0.0020. The two substrate layers are 0.254 mm thick and make it possible, in comparison with the state-of-the-art device manufactured by means of thicker layers, to improve the radiation efficiency of the antenna by around 20%. It is thus advantageous for such a layer to be between 0.1 and 0.6 mm thick, preferably between 0.2 and 0.3. They are separated by two layers of Prepreg Astra-MT77 as well as by layers of copper. In addition, vias make the connections between the different layers of the substrate. Once assembled, all of the layers forming the substrate are 0.8 mm thick. Of course, the types of layers and their number could be different.

B—The Patches

In the following, as in the rest of the detailed description, we will write either "antenna" or "patch" to designate a radiating element 28 of the antenna network (or array).

Figure 13:
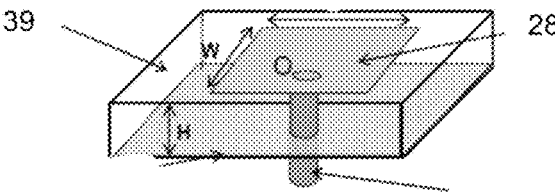
FIG. 13 is a diagram of a radiating patch according to an embodiment of the invention.

The radiating elements 28, one of which is shown diagrammatically in FIG. 13, are flat patches whose surface is 1*1.6 mm. The dimensions of their central opening is 0.9*0.18 mm. Illustrated in FIG. 14, they are spaced apart from each other by 2.4 mm along the longitudinal axis of the module, that is to say the half-wavelength at a frequency of 61.25 GHz, and 2.6 mm in width. Indeed, a distance close to half a wavelength in a vacuum makes it possible to improve the homogeneity of the radiation as well as its efficiency. Of course, small variations in distance have no significant effect, but it is considered that it is preferable that the antennas 28 are separated by a distance ranging from 2.3 to 2.5 mm.

On a printed circuit comprising an ASIC 26 and eight antennas 28, these antennas are thus able to expose to electromagnetic waves between 0.625 and 1 $cm^2$ of the surface of the skin. Since each module 22 (or 24) comprises two circuits and therefore sixteen antennas, an electromagnetic wave emission module is able to emit on a surface ranging from 1.25 to 2 cm². Since the device 10 comprises two modules (22 and 24), it can expose to the waves at least 2.5 square centimeters of the skin, which is a sufficient surface to generate a therapeutic effect according to the scientific literature, in particular for the treatment of chronic pain. In addition, one of the two modules 22 or 24 can be deactivated in order to determine whether the therapeutic effect can persist in the patient while saving energy. In this case, only 1.25 square centimeters of skin are thus exposed to the waves. We can consider a minimum exposure of 1 square centimeter, from which a therapeutic effect can be felt.

Figure 14:
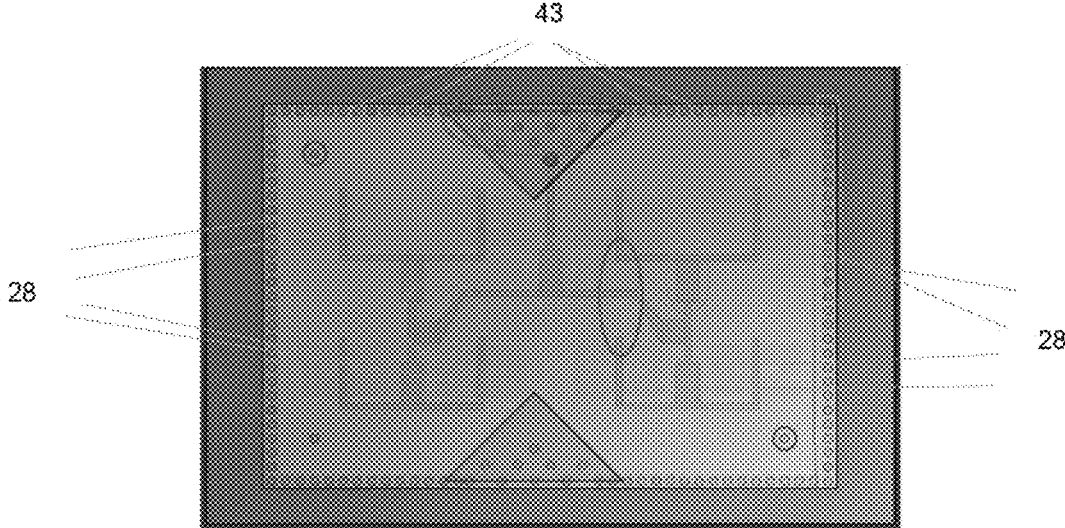
FIG. 14 is a distribution diagram of an antenna network according to the invention.

In addition, as illustrated in FIG. 14, vias 43 are present along the borders of the circuit, thus forming walls of vias 43. Their diameter is 200 micrometers each, and their pitch—the distance separating the respective centers of each via—is 400 micrometers. These vias walls 43 form a cavity, the resonant frequency of which may fall in the frequency band used by the module. To avoid this, it may be necessary to vary the location of certain vias, which the skilled person will be able to do. It is particularly useful for the resonance frequency of the cavity to differ from the frequency band from 55 to 65 GHz, which is a frequency band which is particularly useful in the context of the invention.

C—The Radome

Figure 12:
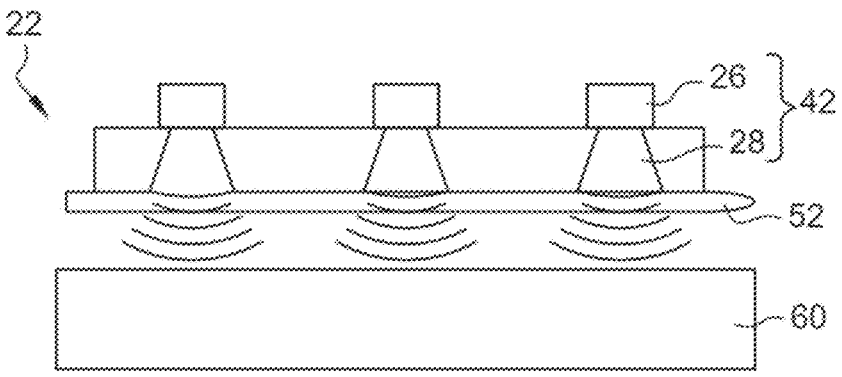
FIG. 12 is a diagram of a wave emission module according to an embodiment of the invention.

Referring to FIG. 12, each patch 28 radiates waves to a skin 60 of the patient, through a radome 52. By "radome" is meant any element of an antenna, an antenna array, network or a radiating patch, having a surface intended to cover a user's skin. It can also be called a "cap" or a "cover". In the field of antennas, radomes are thus the covers of the radiating elements. Since FIG. 12 is schematic and not to scale, the space between the radome 52 and the skin 60 does not exist when the device is normally worn by the user. Besides, one of the goal of the invention is to avoid generating air gap between the antenna and the skin. Therefore, in the context of the invention, it is advantageous that this radome 52 is made of a bio-compatible material, since it is brought into contact with the patient's skin. This radome 52 is here made of polycarbonate and its particularity is that it is designed to adapt the impedance of the antenna to that of the skin 60. Here is why: by default, without a radome, the antenna is designed to radiate in air. When we test the antenna, we do it in the air and it is therefore, without radome 52, suitable for these tests. But within the framework of the invention, the antenna is intended to radiate towards human skin. The radome, which, in the device of the state of the art, is only present to protect the antenna, plays here the role of adapter of impedance. Thus, it aims to adapt the impedance of the antenna, designed to radiate in the air (whose impedance is of the order of 377 ohms which is the impedance in empty space), to that of the skin, whose complex permittivity is about 8-11 j. The permittivity of the radome material, as well as the chosen thickness, makes it possible to adapt the antenna to the impedance of the skin in order to maximize the energy transmitted from the antenna to the skin. This is described below.

To achieve this impedance adaptation, the polycarbonate radome can be made as here, but we could also use other biocompatible materials having an adequate impedance, such as the polyoxymethylene copolymer. The choice depends in particular on the dissipation factor values and the dielectric constant of the material at the frequency most used by the module. Thus, to best adapt the antenna impedance to that of dry skin, tests have shown that the thickness of a polycarbonate radome should be 0.6 mm or 2.0 mm, given that at 61.25 GHZ, its dielectric constant is 2.8 and its dissipation factor is 0.01. With the polyoxymethylene copolymer, the thickness of the radome should be either 0.5 mm or 1.7 mm, the dielectric constant being 3.8, the dissipation factor being between 0.006 and 0.18. Other values are of course possible: more generally, it is advantageous for this radome to have a dielectric constant value less than or equal to 4, and a dissipation factor less than or equal to 0.2, so as to approach an adaptation of optimal impedance. The smaller the thickness, the lower the transmission losses. Here, we therefore chose polycarbonate with a thickness of 0.6 mm, this thickness also being suitable for injection molding techniques. Furthermore, it would be possible, while retaining the same impedance matching, to add to this radome a thickness value about a multiple of 1.4, corresponding to the half-wavelength within the polycarbonate at a frequency of 61.25 Ghz. Indeed, in this case, the impedance adaptation remains identical.

The invention is not limited to the embodiments presented and other embodiments will be apparent to those skilled in the art.

In particular, the wave emission module described can be used in devices other than a bracelet or wristwatch, or in a bracelet adapted to another zone than the wrist, for example around an ankle or any other place. Furthermore, another type of antenna than that described here can be incorporated into this device.

Symmetrically, the antenna elements described here can be integrated into any other type of module or device, and not only to the wave emission module described.

However, the association of modules with this antenna network makes it possible to significantly improve the performance of the wave emission device which integrates them.

Finally, the module can be intended for applications other than the treatment of pain. Indeed, the emission of millimeter waves can in particular be intended to reduce stress or anxiety or more generally to generate a feeling of well-being.

What is claimed is:

1. Patch antenna (28) for a near field radiation, comprising an element (52) having a surface intended to cover a skin of a user (1), the element (52) being arranged to make the impedance of the antenna (28) matching an impedance of skin.

2. Patch antenna (28) according to claim 1, wherein the element (52) comprises, when an electromagnetic wave crosses the element (52) at a frequency of 61.25 gigahertz, an intrinsic impedance value situated between the intrinsic impedance value of air and the intrinsic impedance value of the dry skin deduced from its complex permittivity of 8-j11.

3. Patch antenna (28) according to claim 1, wherein the element (52) comprises a bio-compatible material.

4. Patch antenna (28) according to claim 1, wherein the element (52) comprises only polycarbonate, a thickness value of the element (52) being situated between 0.5 mm and 3 mm plus an integer multiple of a half wavelength when the electromagnetic wave crosses the element.

5. Patch antenna (28) according to claim 1, wherein the element (52) comprises a dielectric constant value less or equal to 4 and a dissipation factor less or equal to 0.2.

6. Patch antenna (28) according to claim 1, comprising a main surface value equal or less than 10 cm².

7. Patch antenna (28) according to claim 1, comprising at least eight patch devices (28) to radiate electromagnetic waves, the at least eight patch devices being situated on a same substrate (39) and separated from each other by a distance value situated between 2.4 and 2.5 mm, the at least eight patch devices being able to expose to electromagnetic radiation between 0.625 cm$^2$ and 1 cm$^2$ of a continuous surface.

8. Patch antenna (28) according to claim 1, comprising a printed circuit board (26) having a substrate, the substrate comprising a dielectric constant value between 2.9 and 3.1 and a dissipation factor value between 0.0010 and 0.0020 when an electromagnetic wave crosses the element at a frequency of 61.25 gigahertz, a thickness value of a layer of the substrate having a thickness value between 0.1 and 0.6 mm, a total substrate assembled thickness being situated between 0.5 and 1.6 mm.

9. Patch antenna (28) according to claim 8, comprising via fences (43) at all the borders of the substrate, the vias (43) of the fences having a diameter value greater than or equal to 175 micrometers, a pitch value between vias being superior or equal to 300 micrometers.

10. Patch antenna (28) according to claim 9, wherein, a cavity being formed by the via fences, the cavity is arranged such that a resonant frequency value of the cavity is outside a frequency range going from 55 to 65 gigahertz.

* * * * *